(12) United States Patent
Zuo et al.

(10) Patent No.: US 8,431,773 B2
(45) Date of Patent: Apr. 30, 2013

(54) PROMOTION OF SOMATIC EMBRYOGENESIS IN PLANTS BY WUSCHEL GENE EXPRESSION

(75) Inventors: Jianru Zuo, New York, NY (US); Qi-Wen Niu, Staten Island, NY (US); Giovanna Frugis, Rome (IT); Nam-Hai Chua, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 13/347,839

(22) Filed: Jan. 11, 2012

(65) Prior Publication Data

US 2012/0102594 A1 Apr. 26, 2012

Related U.S. Application Data

(62) Division of application No. 13/164,904, filed on Jun. 21, 2011, now Pat. No. 8,101,821, which is a division of application No. 12/888,636, filed on Sep. 23, 2010, now Pat. No. 7,977,534, which is a division of application No. 12/722,981, filed on Mar. 12, 2010, now Pat. No. 7,816,580, which is a division of application No. 10/956,120, filed on Oct. 4, 2004, now Pat. No. 7,700,829, which is a division of application No. 09/984,274, filed on Oct. 29, 2001, now abandoned.

(51) Int. Cl.
*C12N 15/82* (2006.01)
*A01H 1/00* (2006.01)

(52) U.S. Cl.
USPC .................... 800/278; 800/290; 800/287

(58) Field of Classification Search .................. None
See application file for complete search history.

(56) References Cited

U.S. PATENT DOCUMENTS

| 7,348,468 | B1 * | 3/2008 | Cahoon et al. ............... 800/278 |
| 2003/0226173 | A1 | 12/2003 | Ratcliffe et al. | |
| 2004/0166563 | A1 | 8/2004 | Lowe et al. | |

FOREIGN PATENT DOCUMENTS

| WO | WO 00/24914 | 5/2000 |
| WO | WO 01/23575 A2 | 4/2001 |

OTHER PUBLICATIONS

Aoyama, T. et al. (1997). "A glucocorticoid-mediated transcriptional induction system in transgenic plants," *The Plant Journal* 11(3):605-612.
Bowman et al., Development 126:2387-2396, 1999.
Doan, D.N. et al., Isolation of molecular markers from the barley endosperm coenocyte and the surrounding nucellus cell layers, *Plant Mol. Biol.* [Medline], 31(4):877-86, 1996.
Gallois, J-L. et al. (2002). "Combined Shoot Meristemless and Wuschel trigger ectopic organogenesis in *Arabidopsis*," *Development* 129:3207-3217.
Kano-Murakami et al., FEBS 334:365-368, 1993.
Mayer, K.F., Role of Wuschel in regulating stem cell fate in the *Arabidopsis* shoot meristem, *Cell* [ GenBank], 95(6):805-815, 1998.
Ohad, N. et al., Mutations in FIE, a WD polycomb group gene, allow endosperm development without fertilization, *Plant Cell* [MEDLINE], 11(3):407-, 1999.
Schoof et al. Cell, 100:635-344, 2000.
Siegfried et al., Development 126:4117-4128, 1999.
Zou et al., The Plant Journal 24(2):265-273, 2000.
Kamiya et al. (2003, The Plant Journal 35:429-441).
Nardmann et al. (2006, Mol. Biol. Evol. 23(12):2492-2504).
Zuo, J. et al., "The Wuschel gene promotes vegetative-to-embryonic transition in *Arabidopsis*," The Plant Journal, vol. 30, No. 3, 2002, pp. 349-359, XP002313477, the whole document.

* cited by examiner

*Primary Examiner* — Stuart F Baum
(74) *Attorney, Agent, or Firm* — Rothwell, Figg, Ernst & Manbeck

(57) ABSTRACT

The present invention relates to methods for promoting somatic embryogenesis from a tissue or organ of a plant, by overexpressing a Wuschel gene in said tissue or organ. In one embodiment, such overexpression can be used as a silent selectable marker for transgenic plants. In another embodiment, such expression can be used to confer apomixis to a plant. In another embodiment, such overexpression can be used to create haploid plants, which can be used to produce dihaploid plants.

8 Claims, 11 Drawing Sheets

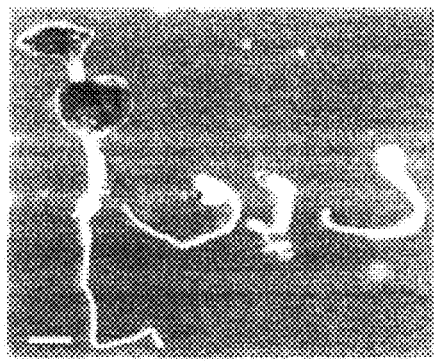 
FIGURE 4A  FIGURE 4B
 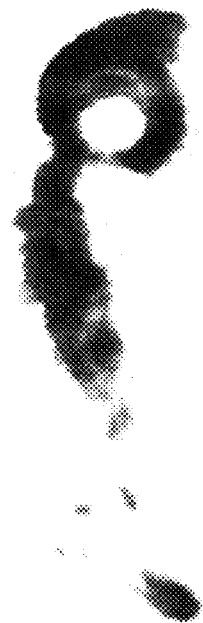
FIGURE 4C  FIGURE 4D

SEQUENCE LISTING

```
<160> NUMBER OF SEQ ID NOS: 15

<210> SEQ ID NO 1
<211> LENGTH: 25
<212> TYPE: DNA
<213> ORGANISM: Artificial
<220> FEATURE:
<223> OTHER INFORMATION: oligonucleotide primer

<400> SEQUENCE: 1
cttatttacc gttaacttgt gaaca                                           25

<210> SEQ ID NO 2
<211> LENGTH: 26
<212> TYPE: DNA
<213> ORGANISM: Artificial
<220> FEATURE:
<223> OTHER INFORMATION: oligonucleotide primier

<400> SEQUENCE: 2
cacataacga gagataacta gttaac                                          26

<210> SEQ ID NO 3
<211> LENGTH: 462
<212> TYPE: DNA
<213> ORGANISM: Zea mays

<400> SEQUENCE: 3
gaggaagatc ccggaagcaa ccaaatcaga agcagaagct agagctacta gttttttgcat     60 tagcaagcag cagcgcagct atagcttctt gcactcgacc atcgatcgct acaaaccaca    120
catatagctg aagcaaatat atccacttgc ttaactggcg gtgtagtgta gctgcgatcg    180
ctgcaaacta cagggtgtag tgatcgtcga tcggctacat atcatatacc atggaggcgc    240
tgagcgggcg ggtaggcgtc aagtgcgggc ggtggaaccc tacggcggag caggtgaagg    300
tcctgacgga gctcttccgc gcggggctgc ggacgcccag cacggagcag attcagcgca    360
tctccaacca actcagcgcc tttgggaagg gggagaacaa aaacgtcctc ctaacgggtc    420
caaaacaaaa aggccgcgag cggcaacaac aaaagaagcg cc                      462

<210> SEQ ID NO 4
<211> LENGTH: 1338
<212> TYPE: DNA
<213> ORGANISM: Zea mays

<400> SEQUENCE: 4
gcacgaggag gaagatcccg gaagcaacca aatcagaagc agaagctaga gctactagtt     60
tttgcattag caagcagcag cgcagctata gcttcttgca ctcgaccatc gatcgctaca    120
```

```
aaccacacat atagctgaag caaatatatc cacttgctta actggcggtg tagtgtagct    180
gcgatcgctg caaactacag ggtgtagtga tcgtcgatcg gctacatatc ataccatg      240 gaggcgctga gcgggcgggt aggcgtcaag tgcgggcggt ggaaccctac ggcggagcag    300
gtgaaggtcc tgacggagct cttccgcgcg ggctgcgga cgcccagcac ggagcagatc     360
cagcgcatct ccacccacct cagcgccttc ggcaaggtgg agagcaagaa cgtcttctac    420
tggttccaga accacaaggc ccgcgagcgc caccaccaca agaagcgccg ccgcggcgcg    480
tcgtcgtcct cccccgacag cggcagcggc aggggaagca caacgagga agacggccgt    540 ggtgccgcct cgcagtcgca cgacgccgac gccgacgccg acctcgtgct gcaaccgcca    600
gagagcaagc gggaggccag aagctatggc caccatcacc ggctcgtgac atgctacgtc    660
agggacgtgg tggagcagca ggaggcgtcg ccgtcgtggg agcggccgac gagggaggtg    720
gagacgctag agctcttccc cctcaagtcg tacggcgacc tcgaggcggc ggagaaggtc    780
cggtcgtacg tcagaggcat cgccgccacc agcgagcagt gcagggagtt gtccttcttc    840
gacgtctccg ccggccggga tccgccgctc gagctcaggc tctgcagctt cggtccctag    900
cagtagcagc tgatcgaccg tcgacgcatg catgcacgta ctgcgtgctg ctgtgcagtg    960
gccttgtcga acgcatcatt gtgtagtcct tgggttctag ctaataccga catgaaaaga   1020
tgtgtgagat gtggaaatac gcatatatat aagctgtaga acgtacgtac gtacgcgcgt   1080
agtatcgctg ccctaccaaa cgacgtacgt tgcataaaga atctgagagg gtcagggaat   1140
gagcatgcag ctgctgctga gatttcaact gcccttttcg ctgatctttt catcatgagg   1200
ccggatgcgc tgcgtgccac ttttttttc gttcatttat gctggtctgt gccctcatgc   1260
atggcatata cggaaattaa ttaacctttg tgctccctaa aaaaaaaaa aaaaaaaaa     1320 aaaaaaaaa aaaaaaaa                                                  1338

<210> SEQ ID NO 5
<211> LENGTH: 720
<212> TYPE: DNA
<213> ORGANISM: Zea mays

<400> SEQUENCE: 5
atggcggcca atgcgggcgg cggtggagcg ggaggaggca gcggcagcgg cagcgtggct     60
gcgccggcgg tgtgccgccc cagcggctcg cggtggacgc cgacgccgga gcagatcagg    120
atgctgaagg agctctacta cggctgcggc atccggtcgc ccagctcgga gcagatccag    180
cgcatcaccg ccatgctgcg gcagcacggc aagatcgagg caagaacgt cttctactgg     240 ttccagaacc acaaggcccg cgagcgccag aagcgccgcc tcaccagcct cgacgtcaac    300
gtgcccgccg ccggcgcggc ggacgccacc accagccaac tcggcgtcct ctcgctgtcg    360
tcgccgccgc cttcaggcgc ggcgcctccc tcgcccaccc tcggtttata cgccgccggc    420
aatgcggccg gatcggctgt gctgctggac acgagttccg actggggcag cagcggcgct    480
gccatggcca ccgagacatg cttcctgcag gtcggtgctg tagtacgttc ttttcttggg    540
cattgcgcgc agtttcacgt tcgtacgtac gagttgatcg ccgcgtcgtt ccatccaccg    600
gtatatataa ctgttaggta cggcggtgcg cgcccgcagg actacatggg cgtgacggac    660
acgggcagct cgtcgcagtg gccacgcttc tcgtcgtcgg acacgataat ggcggcggcc    720

<210> SEQ ID NO 6
<211> LENGTH: 767
<212> TYPE: DNA
<213> ORGANISM: Zea mays
```

-continued

<400> SEQUENCE: 6

```
ccacgcgtcc gagctaggtc acagaagcgc tcaggaaggc cgctgagata gaggcatggc    60
ggccaatgcg ggcggcggtg gagcgggagg aggcagcggc agcggcagcg tggctgcgcc   120
ggcggtgtgc cgcccagcg gctcgcggtg gacgccgacg ccggagcaga tcaggatgct   180
gaaggagctc tactacggct gcggcatccg gtcgcccagc tcggagcaga tccagcgcat   240
caccgccatg ctgcggcagc acggcaagat cgagggcaag aacgtcttct actggttcca   300
gaaccacaag gcccgcgagc gccagaagcg ccgcctcacc agcctcgacg tcaacgtgcc   360
cgccgccggc gcggccgacg ccaccaccag ccaactcggc gtcctctcgc tgtcgtcgcc   420
gccgccttca ggcgcggcgc ctccctcgcc caccctcggc ttctacgccg ccggcaatgg   480
cggcggatcg gctgtgctgc tggacacgag ttccgactgg ggcagcagcg cgctgccat   540
ggccaccgag acatgcttcc tgcaggtcgg tgctgtagta cgttcttttc ttgggcattg   600
cgcgcagttt cacgttcgta cgtacgagtt gatcgccgcg tcgttccatc caccggtata   660
tataactgtt aggtacggcg gtgcgcgccc gcaggactac atgggcgtga cggacacggg   720
cagctcgtcg cagtggccac gcttcgcgtc gtcggacacg ataatgg                 767
```

<210> SEQ ID NO 7
<211> LENGTH: 1367
<212> TYPE: DNA
<213> ORGANISM: Zea mays

<400> SEQUENCE: 7

```
ccacgcgtcc gcctcgatcc atcacctttg catagcatat atagcgcagc agctcgacga    60
aacaccatct catcacatca catcagagca gagcagagca gagcatcacc cgatcccgat   120
cccgctattc ccagccttca gtagcagcag cagtacgtcg cgccctgccc atcgatccat   180
ctggctatca tacctgtcga catggaaggc ggactgagcc cggagcggca cgcggcggcg   240
gagccggtgc ggtcgcggtg gacgcccaag ccggagcaga tactcatcct cgagtccatc   300
ttcaacagcg gcatggtgaa cccgcccaag gacgagacgg tccgcatccg caagctgctg   360
gagcgcttcg gcgccgtggg cgacgccaac gtcttctact ggttccagaa ccgccgctcc   420
cgctcccgcc ggcgccagcg ccagctgcag gcgcaggcgg cggcctcctc gtcctcgtcg   480
ggatcgcccc ccacgagcgg cctcgcaccg ggacacgcga cggcttcgtc gacggcgggg   540
atgttcgcgc acggcgccac ctacggctcg tccgcgtccg cgtcctggcc gccgccgccg   600
tcgtgcgagg ggatgatggg cgacctggac tacggcggcg cgacgacct gttcgccatc   660
tcgcggcaga tgggctacgc cagcggcggt ggctccggct ccgcgtcctc ggcggccgtc   720
gcccaccacg agcagcagca gcagctttac tactcgccgt gccagccagc gagcatgacg   780
gtgttcatca atggcgtggc gacggaggtg ccgcggggc cgatcgacct gcggtccatg   840
ttcgggcagg acgtgatgct ggtgcactcc accgccggcc tcctcccgt caacgagtac   900
ggcgtgctca cgcagagcct gcagatgggc gagagctact tcctggtcac gagggggctac   960
taggtagcta gctatagcac attgcattgc cgacatggag accccagagc tagctgatgc  1020
agtacacgta ctcctcctta ccatgcatgg aattggatgt tattcggatc gtcggagacg  1080
catgcatgca ttgcatgctg cagtacctag tatctctgtc tctgtgtacg tgttcttcag  1140
tgaatgtctg tcagctcttg ccgtccgtcc gtccgtccgg tgtagatcag aaaaaggagg  1200
caaagaattc gataccagca gtgtgtgtgt gtgtgtttac tatatataaa gagagagaca  1260
cacacaaaca aatagagtgt tgtacctacg acgcatccac atcgaacatc tatactaagt  1320
```

```
atgtatgtaa tgatgaatca aaaaaaaaaa aaaaaaaaaa aaaaaag                      1367
```

<210> SEQ ID NO 8
<211> LENGTH: 513
<212> TYPE: DNA
<213> ORGANISM: Zea mays
<220> FEATURE:
<221> NAME/KEY: misc_feature
<222> LOCATION: (1)..(513)
<223> OTHER INFORMATION: n is not known

<400> SEQUENCE: 8

```
gcggtacgcg tgggcgtacc aaggtagcag gtggccgtgc tggaggggct gtacgaacac          60
ggnctgcgca ccccccagcgc ggagcagata cagcagatca cgggcaggct gcgggagcac        120
ggcgccatcg agggcaagaa cgtcttctac tggttccaga accacaaggc ccgccagcgc        180
cagangcagn aagcaggaca gcttcgccta cttcagcagg ctcctccgcc ggccccccgcc       240
gctgccgtg ctctccatgc cccccgcgcc accgtaccat cacgcccgcg tcccggngcc        300
gcccgcgaat accgatgccg attggcgccg ccgccgcccg ctngcattgc aaacgaacaa       360
cngggggngc gcgttttat cttacangaa acccattcta ctttgctgcc ccgcaagggc       420
cccctgcaaa tgccgcctaa taantacccc aagcacagca acaacaacaa caagnaggtn       480
aaagtcnttt tccattnccc aaaaatggaa gtt                                      513
```

<210> SEQ ID NO 9
<211> LENGTH: 1194
<212> TYPE: DNA
<213> ORGANISM: Zea mays

<400> SEQUENCE: 9

```
ccacgcgtcc gcggacgcgt gggcgaccaa ggagcaggtg gccgtgctgg aggggctgta         60
cgagcacggc ctgcgcaccc ccagcgcgga gcagatacag cagatcacgg gcaggctgcg        120
ggagcacggc gccatcgagg gcaagaacgt cttctactgg ttccagaacc acaaggcccg        180
ccagcgccag aggcagaagc aggacagctt cgcctacttc agcaggctcc tccgccggcc        240
cccgccgctg cccgtgctct ccatgccccc cgcgccaccg taccatcacg cccgcgtccc        300
ggcgccgccc gcgataccga tgccgatggc gccgccgccg cccgctgcat gcaacgacaa        360
cggcggcgcg cgtgtgatct acaggaaccc attctacgtg gctgcgccgc aggcgccccc        420
tgcaaatgcc gcctactact acccacagcc acagcagcag cagcagcagc aggtgacagt        480
catgtaccag taccccgagaa tggaggtagc cggccaggac aagatgatga ccagggccgc        540
ggcgcaccag cagcagcagc acaacggcgc cgggcaacaa ccgggacgcg ccggccaccc        600
cagccgcgag acgctccagc tgttcccgcc tccagcccac cttcgtgctg cggcacgaca        660
agggcgcgc cgccaacggc agtaataacg actccctgac gtcgacgtcg acggcgactg        720
cgacagcgac agcgacagcg acagcgtccg cttccatctc cgaggactcg gatgcctgg        780
agagcggcag ctccggcaag ggcgtcgagg aggcgcccgc gctgccgttc tatgacttct        840
tcgggctcca gtcctccgga ggccgctgat catgggactg aggtagagcg agctcgagtg        900
atgaaagccg agccagacgt tcgtgtgatc tcgagtcgtc gtcgatggac ccggttgccg        960
ttgccttttg ttgggttatt gcatgcatgg tgtgcttcat caactactgg aagaagcctg       1020
tgccgatcga accaaaacag tttgcattgt tgagttccgt accgtcctgt agcaacaatg       1080
tagcggagaa atgctactag tagcttcttt ttaaaaaaaa aaaaaaaaaa aaaaaaaaaa       1140
aaaaaaaaaa aaaaaaaaaa aaaaaaaaaa aaaaaaaaaa aaaaaaaaaa aaag             1194
```

<210> SEQ ID NO 10
<211> LENGTH: 506
<212> TYPE: DNA
<213> ORGANISM: Zea mays
<220> FEATURE:
<221> NAME/KEY: misc_feature
<222> LOCATION: (1)..(506)
<223> OTHER INFORMATION: n is not known

<400> SEQUENCE: 10

```
caacaagcta gtactagang atggagagta gtcacagtac tgcagaggat gagagtggat      60
ggaaaggatc aagtggtgct cattcatcag tttcacgatg gagtcctaca aaggagcaaa     120
tagacatgtt ggagaacttt tacaagcagg gaataaggac tcccagcact gagcaaatac     180
aacagattac ctctaggctt agggcttatg gttacatcga gggaaaaaat gtcttctact     240
ggtttcaaaa tcacaaagcg cgccaaagac agaagctcaa gcagaagcaa caaagcattg     300
catactgcaa ttgctttctt catgcctccc accccatttg ccaaaatgtt gtctgcgtcc     360
atattgtttg caaagagtg gattcagctt ttatcctcac caaccaaagg tgcttgcaag     420
tgtaggtatt agctcaaggg attgagactg gtcctttgg catgctaaag aatatgtgat     480
ggcatgcann agtgaacacc cggatt                                          506
```

<210> SEQ ID NO 11
<211> LENGTH: 844
<212> TYPE: DNA
<213> ORGANISM: Zea mays

<400> SEQUENCE: 11

```
gcacgagagt cacagtactg cagaggatga gagtggatgg aaaggatcaa gtggtgctca      60
ttcatcagtt tcacgatgga gtcctacaaa ggagcaaata gacatgttgg agaacttta     120
caagcaggga ataaggactc ccagcactga gcaaatacaa cagattacct ctaggcttag     180
ggcttatggt tacatcgagg gaaaaaatgt cttctactgg tttcaaaatc acaaagcgcg     240
ccaaagacag aagctcaagc agaagcaaca aagcattgca tactgcaatt gctttcttca     300
tgcctcccac cccatttgcc aaaatgttgt ctgcgctcca tattgtttgc aaaagagtgg     360
attcagcttt tatcctcacc aaccaaaggt gcttgcaagt gtaggtatta gctcaaggat     420
tgagactggg tcctttggca tgctaagaat atgtgatggc atgcagagtg aacacccgga     480
ttataactat agcaccagta accgtgaagc cttaactcta tttcctcttc atccaaccgg     540
tattttggaa gaaaaaacaa ctcatcactc tgttgatgtc accgacaaat cttttgtttc     600
tattgctgtt gacgaaaatg gtcatcttgg aaatcaaccc tgctttaatt ttcagtactg     660
aagaacgaag gtatcgagat agtgattaag tatcatcgac caaaactact aacactgtac     720
tactactttc tttgagtagc tcgttgttca tcttcgaaat gagttttatc taattggata     780
ttgagtttaa cgtagtaaaa aaaaaaaaa aaaaaaaaa aaaaaaaaa aaaaaaaaa         840
aaaa                                                                  844
```

<210> SEQ ID NO 12
<211> LENGTH: 741
<212> TYPE: DNA
<213> ORGANISM: Glycine max

<400> SEQUENCE: 12

```
gcacgagaac aagctagtac tagaagatgg agagtcacag tagtgatgct gaggcggaga      60
atgtaaggac tcattcatca gtttcacggt ggagtcctac aaaggagcaa atagacatgt     120
```

```
tagagaacct ttacaagcag ggaataagga ctcccagcac tgagcaaata caacagatta      180
cctctaggct cagggcttat ggtcacatcg agggaaagaa tgtcttctac tggtttcaaa      240
atcacaaagc tcgtcaaaga cagaagctga tgaagcaaca aaccattgca tattccaatc      300
gctttcttcg tgcctcccac cccatttgcc aaaatgttgc ctgcgctcca tattgtttgc      360
aacggagtgg attcagcttt tatcctcaac aatcgaaggt gcttgcaagt ggaggtataa      420
gttcaactgg gcctttaggc atgcaaagaa tgtttgatgg catgcagagt agtgaacacc      480
cggattgtaa ccgtgaagtc ttaactctct ttcctcttca tccaaccggc attttgaaag      540
aaaaaacaac tcatcaagtg ccttcccttg cttcaacttc tgttgttgct gttgatgaag      600
atggtcatct tggaaatcag cccttcttta attttttcac tactgaacca aggtcgagag      660
agtgattagg tgttaattgt cattgaccaa aaaacaact aacatggcac tactttgagt       720
aaaaaaaaaa aaaaaaaaa a                                                  741

<210> SEQ ID NO 13
<211> LENGTH: 906
<212> TYPE: DNA
<213> ORGANISM: Glycine max

<400> SEQUENCE: 13
accagctaaa attaagcatg aaggtgcatc agttcgcacg tggattctgg gagcacgaac       60
cctccctcac actcgggtgc aaacgcttac gccccccttgc ccccaagctt ccaacaccg      120 acaccatttc tccacctcat catcctgtta caaccttcga cctcaagagc ttcatcaaac      180
ctgaaagtgc ctccagaaaa cttggaattg gatcctccga tgataatact aataagagag      240
acccatcttc accccagggc caggctgaaa cgcatattcc aggagggaca cggtggaatc      300
cgactcaaga acaaataggg atattggaga tgctgtacag aggagggatg cgaactccga      360
atgctcaaca aatagagcag atcacagcac agcttagcaa gtacggcaag atcgaaggga      420
agaacgtgtt ctattggttc caaaaccaca agcacgcgga gagacagaag cagaagcgta      480
acaacytagg ccttgctcat agtcctcgta ctactctcac cacttcaccc cccttttagtt     540 gttgtgtaat taccactatg gacaccacaa acgggggga agtagtagaa agagaggagg      600
aagatagccc gttgaagaag tgtaggagct gggcgtttga gtacttggaa gaccaaagag      660
aggaggaaca tagaactctg gagctttttcc cattgcaccc ggaaggcaga tgaagggggtt     720 tgttttaatt gtttgaccaa tttaacgaga atatttttta gcttttaatt aattgtttct      780
gaacccttca ggctgattgg aatgtatgtg ctttaattag tttggtttag tttttcatca      840
ctttcttctt tggttgtgtt gggaagaag aaaacacaaa gtcgtctaca aaaaaaaaa       900 aaaaaa                                                                  906

<210> SEQ ID NO 14
<211> LENGTH: 904
<212> TYPE: DNA
<213> ORGANISM: Glycine max

<400> SEQUENCE: 14
cagcatgaag gtgcatcagt tcacacgtgg attaatctgg gagcacgaac ctttcctcac       60
acttggctgc aagagattac gccctcttgc tcccaagctt cccaacacca aaactatcac      120 taccccttc gatctcaaga gcttcatcag gcccgaaagt ggccccagaa aacccgtttc      180
ctctgacgac actaagaagg atccaccttc acccccaaggc cagattgaaa cgcacccagg      240
agggacacgg tggaatccta cgcaagaaca gataggcata ttgagatgt tgtacaaagg       300
```

```
agggatgcga actccgaatg ctcaacagat agagcagatc actgtccagc ttggaaagta    360
cggcaagatc gaagggaaga acgtgttcta ttggtttcag aatcacaaag cacgcgagag    420
acaaaagcag aagcgcagca gccttgcatc ttctcatagt cctcgaactc ccacaattca    480
cagtgttgtt actttggaga caacaagggg ggaagtggta gagagagatc acgaggaaga    540
tagtccgtac aagaagaagt gcaggagatg ggtatttgac tgcttggaag aacaaaacat    600
gtcatcacct tgtgaacaag aggaacatag aactctggag cttttccat tgcacccgga     660
aggcagatga aggggtttga gtttgattga ccatttatct atcatttttc actttgcttt    720
agttccgaat cgcagctgat tattgaatga atgtggttta attaatttgc tttacttttc    780
ttttttcttt gtattgggaa agaagaaaga caaagttgtc tctgatctgt actcttccac    840
ttaatgctat tcctgacttt ggaaccaaaa aaaaaaaaaa aaaactcgga gagagcgaac    900
tagt                                                                 904

<210> SEQ ID NO 15
<211> LENGTH: 1227
<212> TYPE: DNA
<213> ORGANISM: Arabidopsis thaliana

<400> SEQUENCE: 15
atctctttac taccagcaag ttgttttctt gctaacttca aacttctctt tctcttgttc     60
ctctctaagt cttgatctta tttaccgtta actttgtgaa caaaagtcga atcaaacaca    120
catggagccg ccacagcatc agcatcatca tcatcaagcc gaccaagaaa gcggcaacaa    180
caacaacaag tccggctctg gtggttacac gtgtcgccag accagcacga ggtggacacc    240
gacgacggag caaatcaaaa tcctcaaaga actttactac aacaatgcaa tccggtcacc    300
aacagccgat cagatccaga agatcactgc aaggctgaga cagttcggaa agattgaggg    360
caagaacgtc ttttactggt tccagaacca taaggctcgt gagcgtcaga agaagagatt    420
caacggaaca aacatgacca caccatcttc atcacccaac tcggttatga tggcggctaa    480
cgatcattat catcctctac ttcaccatca tcacggtgtt cccatgcaga gacctgctaa    540
ttccgtcaac gttaaactta accaagacca tcatctctat catcataaca agccatatcc    600
cagcttcaat aacgggaatt taaatcatgc aagctcaggt actgaatgtg gtgttgttaa    660
tgcttctaat ggctacatga gtagccatgt ctatggatct atggaacaag actgttctat    720
gaattacaac aacgtaggtg gaggatgggc aaacatggat catcattact catctgcacc    780
ttacaacttc ttcgatagag caaagcctct gtttggtcta gaaggtcatc aagacgaaga    840
agaatgtggt ggcgatgctt atctggaaca tcgacgtacg cttcctctct tccctatgca    900
cggtgaagat cacatcaacg gtggtagtgg tgccatctgg aagtatggcc aatcggaagt    960
tcgcccttgc gcttctcttg agctacgtct gaactagctc ttacgccggt gtcgctcggg   1020
attaaagctc tttcctctct ctctctcttt cgtactcgta tgttcacaac tatgcttcgc   1080
tagtgattaa tgatgcagtt gttatattag tagttaacta gttatctctc gttatgtgta   1140
atttgtaatt actagctaag tatcgtctag gtttaattgt aattgacaac cgtttatctc   1200
tatgatgaat aagttaaatt tatatat                                       1227
```

PROMOTION OF SOMATIC EMBRYOGENESIS IN PLANTS BY WUSCHEL GENE EXPRESSION

CROSS-REFERENCE TO RELATED APPLICATIONS

The present application is a division of U.S. patent application Ser. No. 13/164,904 filed 21 Jun. 2011, which in turn is a division of U.S. patent application Ser. No. 12/888,636 filed 23 Sep. 2010, now U.S. Pat. No. 7,977,534, which in turn is a division of U.S. patent application Ser. No. 12/722,981 filed 12 Mar. 2010, now U.S. Pat. No. 7,816,580, which in turn is a division of U.S. patent application Ser. No. 10/956,120 filed 4 Oct. 2004, now U.S. Pat. No. 7,700,829, which in turn is a division of U.S. patent application Ser. No. 09/984,274 filed 29 Oct. 2001, now abandoned. Each application is incorporated herein by reference.

SEQUENCE SUBMISSION

The present application is being filed along with a Sequence Listing in electronic format. The Sequence Listing is entitled 2312132SequenceListing.txt, created on 6 Jan. 2012 and is 17 kb in size. The information in the electronic format of the Sequence Listing is part of the present application and is incorporated herein by reference in its entirety.

BACKGROUND OF THE INVENTION

Somatic embryogenesis is a unique pathway for asexual propagation or somatic cloning in plants. The developmental process of somatic embryogenesis shares considerable similarity with that of zygotic embryogenesis (Zimmerman, 1993; Mordhorst et al., 1997) and this is likely due to the conservation in the underpinning cellular and molecular mechanisms between the two processes. Therefore, somatic embryogenesis provides an attractive model system for studying zygotic embryogenesis, particularly because zygotic embryos are encased by maternal tissues and difficult to access by biochemical and molecular tools. Moreover, in biotechnological applications, most economically important crop as well as non-crop plants are regenerated via somatic embryogenesis.

In contrast to organogenesis, which requires a high cytokinin to auxin ratio (Skoog and Miller, 1957; Sugiyama, 1999; Sugiyama, 2000), somatic embryogenesis does not require any external cytokinins, but rather is dependent on high concentrations of 2,4-D (Zimmerman, 1993; Mordhorst et al., 1997; Sugiyama, 2000), a synthetic chemical that has long been used as a functional analog of auxin. It is generally believed that somatic embryogenesis is mediated by a signaling cascade triggered by external auxin or 2,4-D (Zimmerman, 1993; Mordhorst et al., 1997; Schmidt et al., 1997). However, very little is known about the signal transduction pathway, particularly the molecular mechanism involved in the transition of a vegetative cell to an embryogenic competent cell.

During the last two decades, considerable efforts have been made to identify genes with altered expression patterns during somatic embryogenesis (Schmidt et al., 1997; Lin et al., 1996; Thomas, 1993). Most of these genes, however, are up-regulated only in late developmental stages, suggesting that they do not play a direct role in the vegetative-to-embryogenic transition. Thus far, the only exception is the carrot Somatic Embryogenesis Receptor-like Kinase (SERK) gene the expression of which appears to mark the vegetative-to-embryogenic transition; however, its function remains unclear (Schmidt et al., 1997). An additional molecular approach was attempted by manipulating certain embryo-specific genes. The Arabidopsis Leafy cotyledon 1 (LEC1) gene, encoding a subunit of the HAP heterotrimeric transcription factor complex (HAP3), has been proposed as a key regulator for embryonic identity (Lotan et al., 1998). Mutations in the LEC1 locus result in defective embryo maturation as well as the conversion of cotyledons into true-leaf-like structures (Lotan et al., 1998; Meinke, 1992; Meinke et al., 1994). Constitutive overexpression of LEC1 leads to severely abnormal plant growth and development with occasional formation of somatic embryo-like structures (Lotan et al., 1998). The developmental fate of these embryo-like structures, however, remained unknown due to the lethality of LEC1 overexpression.

The publications and other materials used herein to illuminate the background of the invention, and in particular, cases to provide additional details respecting the practice, are incorporated herein by reference, and for convenience, are referenced by author and date in the text and respectively grouped in the appended List of References.

SUMMARY OF THE INVENTION

One aspect of the present invention is a method to promote somatic embryogenesis from a tissue or organ of a plant, said method comprising overexpressing a Wuschel gene in said tissue or organ.

A second aspect of the invention is a method to generate somatic plant embryos wherein said method comprises overexpressing a Wuschel gene in a tissue or organ of a plant.

Another aspect of the invention is a method for generating shoots from a tissue or organ of a plant, said method comprising overexpressing a Wuschel gene in said tissue or organ.

Yet another aspect of the invention is a method of selecting plants transformed with a vector comprising a silent selectable marker wherein the marker is a Wuschel gene.

Another object of the invention is a method of producing an apomictic plant line.

Another object of the invention is a method of producing haploid plants.

BRIEF DESCRIPTION OF THE DRAWINGS

FIG. 2E shows an enlarged view of a germinating somatic embryo isolated from the explant shown in (FIG. 2D). FIG. 2F shows a germinating seedling derived from a somatic embryo grown on MS medium (45 days). Scale bar, 100 µm for FIGS. 2A and 2E; 1 mm, for FIGS. 2B, 2C, 2D and 2F.

FIG. 3A shows a pre-embryo stage before the first embryonic cell division (arrows) and a two-cell stage after the first asymmetric division with a smaller apical cell (A) and a larger basal (B) cell. FIG. 3B shows embryos at the globular (G) and the early heart (H) stages. FIG. 3C shows a germinating embryo. C: cotyledon; H: hypocotyl. FIG. 3D shows an abnormal somatic embryo with three cotyledons (C) anchored on the hypocotyl (H). Scale bar, 10 μm for FIG. 3A; 100 μm for FIGS. 3B-D.

FIGS. 4A-H illustrate phytohormone-independent somatic embryo formation caused by the pga6 gain-of-function mutation. FIG. 4A is an overview of pga6 mutant seedlings germinated and grown on MS medium (first seedling from the left) or the inductive MS medium (MST: 5 μM 17-β-estradiol) for 7 days. FIGS. 4B-D show pga6 seedlings that were cultured on the inductive MS medium for 10 days (FIG. 4B), 14 days (FIG. 4C) or 30 days (FIG. 4D). FIGS. 4E-F show seven-day-old pga6 seedlings germinated and grown on MS medium which were transferred onto an inductive MS medium and cultured for 5 (FIG. 4E) or 10 (FIG. 4F) days. FIG. 4G shows pga6 root explants which were cultured on the inductive MS medium for 20 days. FIG. 4H is an enlarged view of FIG. 4G. Scale bar, 1 mm.

FIG. 5A is a schematic diagram illustrating the insertion site of the T-DNA upstream of the WUS gene (not shown to scale). Arrows indicate the directions of transcription. FIG. 5B shows pga6 seeds (T2, homozygous) which were germinated and grown on MS medium supplemented with various concentrations of the inducer as indicated. Ten-day old seedlings are shown. The scale bar represents 1 mm. FIG. 5C shows the expression of PGA6/WUS induced by different concentrations of the inducer. Ten-day-old pga6 seedlings were germinated and grown on MS medium and transferred to an MS medium containing various concentrations of 17-β-estradiol as indicated and were cultured for an additional 16 hours before total RNA extraction. Five μg total RNA were used for Northern blot analysis using a WUS cDNA fragment as a probe. Positions of two RNA molecular weight markers are indicated at the right (GIBCO BRL, catalog number, 15620-016). FIG. 5D shows ethidium bromide staining of the gel as a control for RNA loading and transfer.

FIG. 6A shows embryogenic callus and FIG. 6B shows somatic embryo formation from root tips of XVE-WUS cDNA T2 seedlings grown for 15 days in a medium supplemented with 17-β-estradiol (10 μM). FIGS. 6C-H show 15 day-old T1 35S::WUS seedling phenotypes. FIG. 6C shows the tips of the roots are enlarged and show an embryo-like structure. FIG. 6D shows the adventitious root tip. FIG. 6E shows that WUS overexpression induces both organogenesis and embryogenesis from the root. FIG. 6F shows detail of early embryo structure formation. FIG. 6G shows the shoot apical meristem is dramatically altered and, besides forming lateral organs with altered shaped, givers rise to adventitious shoots and somatic embryos. FIG. 6H shows the entire shoot apical meristem expands and lateral organs transform into meristematic tissues. Scale bar is 1 mm.

DETAILED DESCRIPTION OF THE INVENTION

Figure 1:
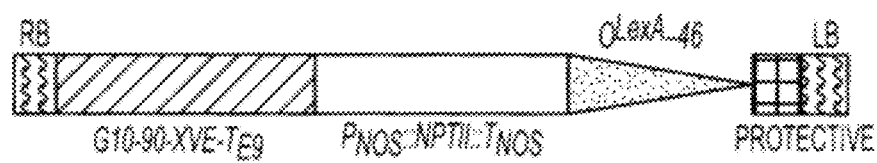
FIG. 1 is a schematic diagram of the XVE activation tagging vector pER16.

To dissect the signaling pathway during somatic embryogenesis, we have employed a genetic approach to identify gain-of-function mutations that can promote embryogenic callus formation from *Arabidopsis* root explants. *Arabidopsis thaliana* is known to be a species difficult for somatic embryogenesis. Thus far, embryogenic calli could only be induced from immature embryos of wild-type (WT) plants or from the primordia timing (pt) mutant plant (Wu et al., 1992; Mordhorst et al., 1998; and references therein). Therefore, *Arabidopsis* vegetative explants appear to be reliable materials for screening for genetic mutations involved in the vegetative-to-embryonic transition. Herein we disclose the identification of the Plant Growth Activator 6 (PGA6) gene by a novel genetic screen. Overexpression of PGA6 promotes the formation of somatic embryos from various vegetative tissues as well as from zygotic embryos independently of any external plant hormones. These somatic embryos, following a developmental process remarkably similar to that of zygotic embryogenesis, are able to germinate and grow into healthy, fertile plants, suggesting that PGA6 is involved in the maintenance of embryonic cell identity. PGA6 was found to be identical to the Wuschel gene (WUS), a homeodomain protein that was previously characterized as a key regulator for specification of meristem cell fate (Laux et al., 1996; see, also, WO 01/23575 regarding WUS homologs (SEQ ID NOs: 3-14)). The nucleic acid and protein sequences of Wuschel are those as shown by GenBank Accession No. AJ012310 (SEQ ID NO:15). Our results reveal an additional function of WUS/PGA6 during embryogenesis, and also open a new avenue in biotechnological applications.

In this study, we identified a genetic locus PGA6 by a novel functional screen aimed at elucidating the molecular mechanism of somatic embryogenesis. A gain-of-function mutation at this locus causes a rapid transition from vegetative or somatic to embryonic cells, leading to somatic embryo development from various tissues and organs. The pga6 mutation-dependent cell fate reprogramming can occur either in the presence or absence of external plant hormones, although the local concentration of endogenous growth regulators might play an important role in the vegetative-to-embryonic transition. In addition, the hormone-independent somatic embryogenesis in pga6 strikingly resembles zygotic embryo development. These observations suggest that PGA6 plays a critical regulatory role during embryogenesis, likely involved in maintaining embryonic cell identity. Molecular and genetic analyses indicate that pga6 is a gain-of-function allele of the previously characterized wus loss-of-function mutation (Mayer et al., 1998).

In addition to causing vegetative tissues or organs to become embryogenic, inducing overexpression of PGA6 in zygotic embryos also results in the generation of somatic embryos at very high frequency, whereas no somatic embryos or embryogenic calli were observed in the absence of the inducer. Wu et al. (1992) previously reported the generation of somatic embryos from isolated *Arabidopsis* zygotic embryos at very low efficiency, which involved tedious multiple subculturing and hormone treatments. Our finding that the simple manipulation of a single gene (WUS) was able to generate somatic embryos at very high frequency is a major advance in plant biotechnology.

Loss-of-function mutations in WUS have been shown to cause impaired development of shoot and floral meristems in *Arabidopsis*, resulting in the absence of the shoot and floral meristems in all developmental stages of wus embryos and adult plants (Laux et al., 1996; Mayer et al., 1998). Genetic studies revealed that WUS interacts with CLAVATA (CLV), and the WITS/CLV self-regulatory loop, in which CLV presumably acts upstream of WUS (Clark, 2001) appears to be critical for the maintenance of stem cell identity (Schoof et al., 2000; Brand et al., 2000; Waites and Simon, 2000). On the other hand, ectopic expression of WUS results in enlarged meristems (Schoof et al., 2000). Collectively, these observations suggested an instructive role of WUS for the specification of meristematic stem cell fate. Interestingly, the WUS gene is not expressed in the stem or meristem cells; rather its expression is restricted to a small group of cells underneath the stem cells during the entire embryogenesis and post-embryogenesis stages (Mayer et al., 1998; Schoof et al., 2000). The cluster of WUS expressing cells was termed as the organizing center (Mayer et al., 1998). The unexpected expression pattern led to postulations that WUS promotes and/or maintains the stem cell fate by a diffusion mechanism or acted in a non-cell-autonomous manner (Mayer et al., 1998; Waites and Simon, 2000).

Our observation that WUS is capable of promoting vegetative-to-embryonic transition and eventually somatic embryo formation uncovers an additional critical function of this homeodomain protein during embryogenesis. Presumably, the highly restrictive expression of WUS hallmarks the putative embryonic organizing center which, in turn, may give rise to stem cells during embryogenesis and later development. Therefore, WUS is involved in promoting and maintaining the identity of embryonic cells from which stem cells are derived. Because WUS-expressing cells have not been morphologically and functionally characterized, it remains of interest to determine whether this cluster of cells indeed represents a functional organizing center similar to Spemann's organizer discovered nearly 80 years ago in Xenopus embryos (Spemann and Mangold, 1924).

Interestingly, the LEC1 transcript was barely detectable in the organizing center or the WUS expressing domain, albeit LEC1 was found to express throughout embryogenesis as well as in seeds (Lotan et al., 1998). Consistent with these observations, somatic embryo expression of LEC1, presumably resembling that in zygotic embryos, was found to be promptly repressed by the WUS activity. In addition, the LEC1 function appeared to require unidentified embryo- and or seed-specific cofactors, since inducible overexpression of LEC1 by the XVE system (Zuo, et al., 2000b) during post-germination stages did not result in any detectable phenotype. By contrast, WUS appears to be a key player in promoting embryonic potential as its activity does not appear to require any developmentally specific factors under our tested conditions. Taken together, these observations further suggest that WUS plays a predominant role in inducing the embryonic potential, whereas LEC1 is likely involved in promoting differentiation of embryonic cells at later developmental stages. A reasonable assumption would be that the LEC1 activity, a driving force for embryo cell differentiation, must be excluded in order to fully maintain the embryonic potential in the putative organizing center.

Recently, Stone et al. (2001) showed that LEC2 encodes a transcription factor containing a B3 domain unique to several other plant transcription factors including ABI3/VP1 and FUS3. Overexpression of LEC2 leads to formation of somatic embryos as well as the formation of callus, cotyledon-like and leaf-like structures, a phenotype similar to that of pga6 mutant, suggesting that LEC2 might be functionally close to WUS. It will be interesting to determine if the LEC2 activity is also dependent on embryo- and/or seed-specific cofactors as in the case for LEC1.

Systems for hormone-dependent somatic embryo formation have been well established in several model species, and rapidly extended to other species (Zimmerman, 1993; Mordhorst et al., 1997). In all these in vitro systems, phytohormones, particularly auxin or 2,4-D, are essential for induction of somatic embryo formation. *Arabidopsis* has been known to be a species difficult for somatic embryogenesis, even though with limited success by using wild-type immature zygotic embryos (e.g., Wu et al., 1992) or certain vegetative tissues of the pt mutant plants (Mordhorst et al., 1998). Overexpression of Leafy cotyledon 1 (Lec1) causes severe developmental abnormality and growth arrest, a phenotype similar to that of the pga6 mutant (Lotan et al., 1998). Formation of somatic embryos is occasionally observed in the Lec1 overexpression plants (Lotan et al., 1998), but these embryos never germinate or develop into normal adult plants. The finding that the pga6 gain-of-function mutation or overexpression of WUS results in hormone-independent somatic embryo formation at a high frequency will have significant impact on plant biotechnology, and provides a convenient and attractive model system for many aspects of plant biological research.

In another embodiment of the invention, embryogenesis is induced in haploid cells, such as pollen cells, to produce haploid plants. This can be achieved by stably transforming a plant cell or tissue with a WUS gene under the control of a tissue specific promoter that is active in a haploid cell or tissue, and expressing the WUS gene therein, or by introducing the WUS gene into a plant tissue or cell under the control of an inducible promoter and applying the inducer to cause expression of the WUS gene therein. In a preferred embodiment, the WUS gene is under the control of a promoter that is both haploid-tissue specific and inducible. In a preferred embodiment, a promoter is used that is both inducible and tissue-specific, giving greater control over the process. In a most preferred embodiment, a WUS gene linked to an inducible pollen-specific promoter is used to induce somatic embryogenesis in pollen cells.

Expression of the gene in the haploid tissue or cell (for example, by application of the inducer specific for the inducible promoter) results in the formation of haploid somatic embryos, which can be grown into haploid plants using standard techniques. When an inducible promoter is used (whether tissue specific or not), a preferred method comprises exposing excised transgenic tissue containing the haploid cells (e.g., pollen or ovules) to the inducer specific for the inducible promoter for a time sufficient to induce the formation of a somatic embryo, withdrawing the inducer, and growing the somatic embryo into a transgenic haploid plant in the absence of the inducer.

Diploidization of the haploid plants to form dihaploids, either spontaneously or by treatment with the appropriate chemical (e.g. colchicine) will significantly expedite the process of obtaining homozygous plants as compared to a method of conventional genetic segregation. This technology will not only be beneficial for breeding purposes but also for basic research such as studies of mutagenesis and other genetic studies, because dihaploids are truly homozygous down to the DNA level, containing two identical copies of each gene.

Additionally, WUS genes will be useful for inducing apomixis into plants. Apomixis and methods of conferring apomixis into plants are discussed in several patents (see, e.g., U.S. Pat. Nos. 5,710,367; 5,811,636; 6,028,185; 6,229,064;

and 6,239,327 as well as WO 00/24914 which are incorporated herein by reference). Reproduction in plants is ordinarily classified as sexual or asexual. The term apomixis is generally accepted as the replacement of sexual reproduction by various forms of asexual reproduction (Rieger et al., IN Glossary of Genetics and Cytogenetics, Springer-Verlag, New York, N.Y., 1976). In general the initiation of cell proliferation in the embryo and endosperm are uncoupled from fertilization. Apomixis is a genetically controlled method of reproduction in plants where the embryo is formed without union of an egg and a sperm. There are three basic types of apomictic reproduction: 1) apospory-embryo develops from a chromosomally unreduced egg in an embryo sac derived from a somatic cell in the nucellus, 2) diplospory-embryo develops from an unreduced egg in an embryo sac derived from the megaspore mother cell, and 3) adventitious embryony-embryo develops directly from a somatic cell. In most forms of apomixis, pseudogamy or fertilization of the polar nuclei to produce endosperm is necessary for seed viability. These types of apomixis have economic potential because they can cause any genotype, regardless of how heterozygous, to breed true. It is a reproductive process that bypasses female meiosis and syngamy to produce embryos genetically identical to the maternal parent. With apomictic reproduction, progeny of specially adaptive or hybrid genotypes would maintain their genetic fidelity throughout repeated life cycles. In addition to fixing hybrid vigor, apomixis can make possible commercial hybrid production in crops where efficient male sterility or fertility restoration systems for producing hybrids are not known or developed. Apomixis can make hybrid development more efficient. It also simplifies hybrid production and increases genetic diversity in plant species with good male sterility.

It would be ideal to find genes controlling obligate or a high level of apomixis in the cultivated species and be able to readily hybridize cross-compatible sexual x apomictic genotypes to produce true-breeding $F_1$ hybrids. In reality, most desirable genes controlling apomixis are found in the wild species which are distantly related to the cultivated species. Although interspecific crosses may be possible between the cultivated and wild species, chromosome pairing between genomes is usually low or nonexistent.

Although apomixis is effectively used in Citrus to produce uniform and disease- and virus-free rootstock (Parlevliet et al, 1959) and in buffelgrass (Bashaw, 1980) and Poa (Pepin et al, 1971) to produce improved cultivars, it has not been successfully transferred to a cultivated crop plant. The transfer of apomixis to important crops would make possible development of true-breeding hybrids and commercial production of hybrids without a need for cytoplasmic-nuclear male sterility and high cost, labor-intensive production processes. An obligately apomictic $F_1$ hybrid would breed true through the seed indefinitely and could be considered a vegetative or clonal method of reproduction through the seed. The development of apomictically reproducing cultivated crops would also provide a major contribution toward the food security in developing nations (Wilson et al, 1992).

The present invention is further detailed in the following Examples, which are offered by way of illustration and are not intended to limit the invention in any manner. Standard techniques well known in the art or the techniques specifically described below are utilized.

EXAMPLE 1

Plant Materials, Growth Conditions and Plant Transformation

The Wassilewskija, Columbia and Landsberg ecotypes of *A. thaliana* were used. Plants were grown under continuous white light at 22° C. on solid A medium (1×MS salts (Murashige and Skoog, 1962), 3% sucrose, 0.8% agar) supplemented with appropriate antibiotics and/or the inducer 17-β-estradiol. Unless indicated otherwise, 5 μM 17-β-estradiol was used for induction. In planta transformation of *Arabidopsis* plants (the Columbia ecotype) was performed as described by Bechtold et al. (1993). Transformation of root explants was carried out according to Koncz et al. (1989).

Light and electron microscope analyses were carried out as previously described (Zuo et al., 2000b).

EXAMPLE 2

Screening of pga Mutants

*Agrobacteria* ABI cells carrying pER16 were used to transform *Arabidopsis* (the Wassilewskija ecotype) root explants. Infected root explants were cultured on the screening medium (SCM; 1×MS salts, 1% sucrose, 0.5 g/L MES (2-[N-morpholino]ethanesulfonic acid), 0.15 mg/L IAA (indole acetic acid), 5 μM 17-β-estradiol, 50 mg/L kanamycin, 100 mg/L carbenicillin and 0.2% phytagel, pH 5.7) at 22° C. under a 16-hour white light/8-hour dark cycle. Putative pga mutants, which appeared as rapidly growing green-yellowish or green cell clumps or calli upon culturing on the SCM for 10-15 days, were transferred onto a non-inductive shoot induction medium (SIM; for green calli; 1×MS salts, 1% sucrose, 0.5 g/L MES, 1 mg/L 2-IP ($N^6$, $\delta^2$-isopentenyladenine), 0.15 mg/L IAA, 50 mg/L kanamycin, 100 mg/L carbenicillin and 0.2% phytagel, pH 5.7) to recover mutant shoots. The green-yellowish calli were transferred onto the callus induction medium (CIM; 1×B5 salts (Sigma), 2% glucose, 0.5 g/L MES, 0.5 mg/L 2,4-D, 0.05 mg/L kinetin, 50 mg/L kanamycin, 100 mg/L carbenicillin and 0.2% phytagel, pH 5.7). After culturing on the CIM for 7-10 days, the amplified calli were then transferred onto a SIM to regenerate shoots. Regenerated shoots, usually formed after culturing on the SIM for 2-3 weeks, were then transferred to a root induction medium (RIM; identical to SIM but without 2-IP) to promote root formation. Whereas most putative pga mutant plantlets, including pga6, were able to set seeds after transferring to soil, a portion of roots were excised and placed on the CIM to reinduce callus formation, followed by repeating the above-described screening procedure to confirm the inducer-dependent pga phenotype. The pga6 mutant was backcrossed with wild-type (Wassilewskija) plants twice for further genetic and phenotypic analyses.

EXAMPLE 3

Molecular Manipulations

Molecular manipulations were performed as specifically stated or by the methods as taught by Sambrook et al. (1989). The XVE inducible expression vector pER10 is identical to pER8 (Zuo et al., 2000a) except that the hygromycin selectable marker of pER8 was replaced with a kanamycin selectable marker. To construct the mutagenesis vector pER16, pER10 was digested with SpeI and Asp7181 followed by Klenow enzyme fill-in reaction and religation. The resulting pER16 vector lacked the rbcsS3A polyA addition sequence of the $O^{LexA-46}$::$T^{3A}$ expression cassette (see FIG. 1 of Zuo et al. (2000a)).

pER16 is shown in FIG. 1. Only the region between the Right Border (RB) and Left Border (LB) is shown (not to scale). Two transcription units and the $O^{LexA}$-46 promoter are located between the RB and LB. In the first transcription unit, the G10-90 promoter (Ishige et al., 1999) drives the XVE fusion gene terminated by the rbcs E9 polyA addition sequence. The second transcription unit consists of the Nopaline Synthase (NOS) gene promoter, the coding sequence of the Neomycin Phosphotransferase II (NPT II) gene and the NOS polyadenylation sequence. The $O^{LexA}$-46 promoter consists of 8 copies of the LexA operator sequence fused to the −46 CaMV35S promoter. Upon integration into the plant genome, the $O^{LexA}$-46 promoter can activate the transcription of sequences fused downstream from the promoter in a 17-β-estradiol-dependent fashion.

The pER16-tagged genomic sequences were recovered by Tail-PCR (Liu et al., 1995), and the purified PCR fragments were directly subjected to DNA sequencing analysis.

The WUS cDNA was amplified from flower cDNA by polymerase chain reaction (PCR), using the primers WusUp (5' CTTATTTACCGTTAACTTGTGAACA 3') (SEQ ID NO:1) and WusLow (5' CACATAACGAGAGATAACTAGT-TAAC 3') (SEQ ID NO:2). The 1062-bp long PCR fragment, harboring the entire protein coding region plus part of the 3' UTR, was first cloned into the pPCR-Script Amp SK(+) vector (Stratagene) and then cut with XhoI (vector polylinker site) and SpeI (site in the 3' UTR of the WUS cDNA) for the subsequent cloning into the corresponding sites of both the pER10 vector (17-β-estradiol inducible) and the pBA002 vector (constitutive 35S promoter) for the 35S::WUS expression. The correct sequence of the WUS cDNA was confirmed by DNA sequencing analysis.

Genomic DNA Southern and RNA Northern blotting analyses were carried out as previously described (Zuo et al., 2000a; Zuo et al., 2001).

EXAMPLE 4

Screening of the Plant Growth Activator Mutants

Explants derived from *Arabidopsis* vegetative tissues are known to be incapable of forming somatic embryos or embryogenic calli promoted by external plant hormones. We presumed that external hormones alone were incapable of activating key regulators of *Arabidopsis* necessary for vegetative-to-embryogenic transition. With appropriate hormone treatments, gain-of-function mutations in these regulatory genes may activate the vegetative-to-embryonic transition. Such gain-of-function mutations, on the other hand, may also cause severe defects during subsequent plant growth and development. Therefore, if the expression of the mutated gene and/or the biological activity of related gene products is not appropriately controlled, it will be difficult to maintain the identified mutations. An example is the constitutive overexpression of the LEC1 gene (Lotan et al., 1998). As a consequence, we carried out the screen by using a previously developed chemical-inducible XVE system, which has been demonstrated to be stringently controlled and to be highly responsive to the inducer 17-β-estradiol, a mammalian hormone with no apparent physiological effects on plant growth and development (Zuo et al., 2000a). The use of an inducible promoter thus allows us to recover normal mutant plants by withdrawal of the inducer, even in the case that the gain-of-function mutation is lethal.

*Arabidopsis* root explants were transformed with *Agrobacteria* (Koncz et al., 1989) carrying an XVE vector pER16 (FIG. 1). Transformed explants were cultured on a screening medium (SCM containing auxin, 17-β-estradiol and kanamycin but without cytokinin). Note that mutations functionally analogous to cytokinin independent 1 (cki1; Kakimoto, 1996) should also be recovered under the screening conditions. In the primary screen, we isolated 35 putative mutants by interrogating approximately 38,000 independent transformation events. As expected, most of these mutants (33 out of 35) showed a cki1-like phenotype, i.e., shoot regeneration independent of cytokinin. The remaining two mutants gave rise to green-yellowish embryogenic calli. We collectively named these two classes of mutations as pga for plant growth activator. Here, we disclose a detailed characterization of one of these mutants which is named pga6.

EXAMPLE 5

Figure 2A:
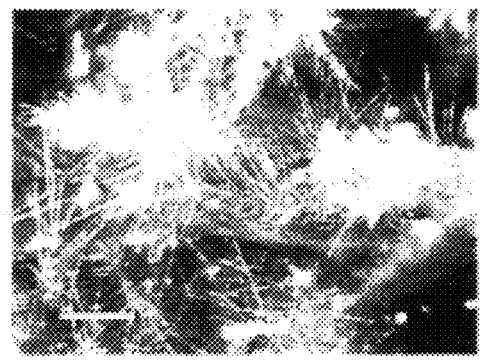
FIGS. 2A-F illustrate the pga6 gain-of-function mutant phenotype. Root explants derived from pga6 seedlings were cultured on the non-inductive SCM (SCM minus 17-β-estradiol) for 20 days (FIG. 2A); or on the inductive SCM for 10 days (FIG. 2B), 20 days (FIG. 2C), or 30 days (FIG. 2D).
Figure 2B:
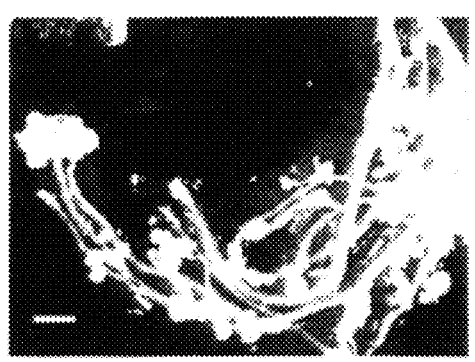
Figure 2C:
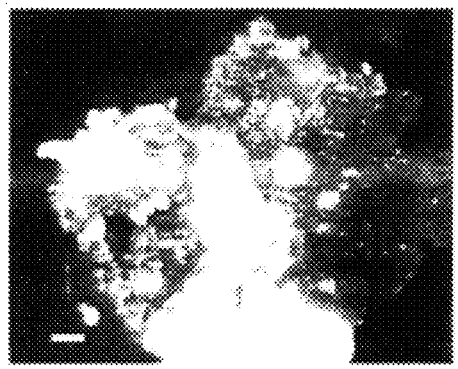
Figure 2D:
Figure 2E:
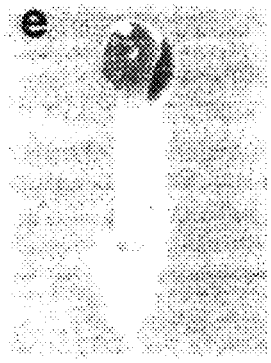

The pga6 Gain-of-Function Mutation Promotes the Vegetative-to-Embryonic Transition The pga6 mutant was initially identified by its ability to form embryogenic calli on SCM. The embryogenic calli were transferred onto a shoot induction medium containing both auxin and cytokinin but without the chemical inducer 17-β-estradiol. After 2-3 weeks, shoots were regenerated from the isolated calli. Explants derived from different organs of the regenerated shoots were cultured on SCM as described before; a portion of the excised explants was cultured in SCM without the inducer to serve as controls. After culturing for 7-10 days, only slowly growing calli were occasionally observed in the absence of inducer (FIG. 2A). In the presence of the inducer, however, the explants produced numerous, rapidly growing, yellowish embryogenic calli (FIG. 2B), which subsequently developed into distinctive somatic embryos (FIG. 2C). After being transferred onto a non-inductive medium, all these somatic embryos were able to germinate (FIGS. 2D and 2E) and develop into fertile adult plants, most of which were morphologically indistinguishable from wild-type plants (FIG. 2F).

Figure 2F:
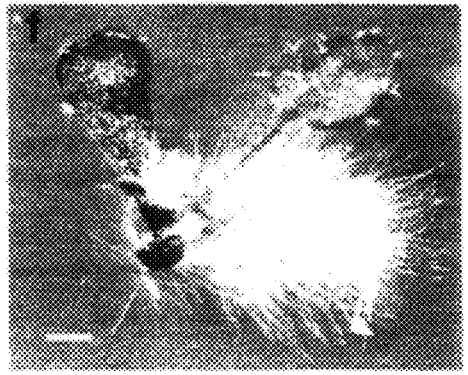

To further confirm the above observations, T1 seeds collected from the T0 somatic embryo-derived plants, as shown in FIG. 2F, were germinated on MS medium in the absence of the inducer. The inducer-dependent somatic embryo formation was reproducibly observed in pga6 explants prepared from different organs/tissues of previously uninduced T1 plants. Similar to that observed in the T0 explants, the highest frequency of somatic embryo formation was observed from root explants, followed by leaf petioles, stems and leaves. Isolated zygotic embryos had a frequency similar to that of root explants. The above results suggested that the pga6 gain-of-function mutation was able to promote vegetative-to-embryonic transition under our experimental conditions, and that the PGA6 gene was most likely tagged by the inducer-responsive $O^{LexA}$-46 promoter.

In addition to the formation of somatic embryos, which are characterized by the presence of cotyledons lacking trichomes on the surfaces, we also observed approximately 10% of the pga6 calli developing into shoots, suggesting that PGA6 is also involved in organogenesis.

EXAMPLE 6

Figure 3A:
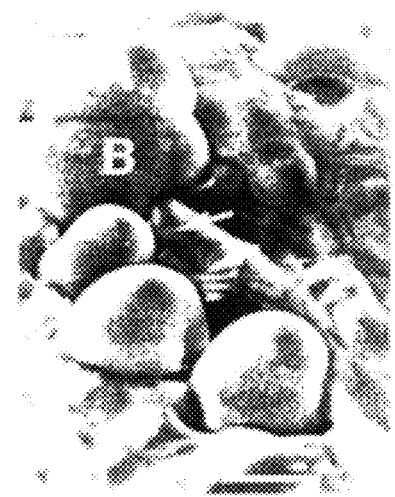
FIGS. 3A-D are electron microscopic analyses showing somatic embryogenesis in pga6 mutant explants (culturing conditions were identical to those shown in FIGS. 2A-F).
Figure 3B:
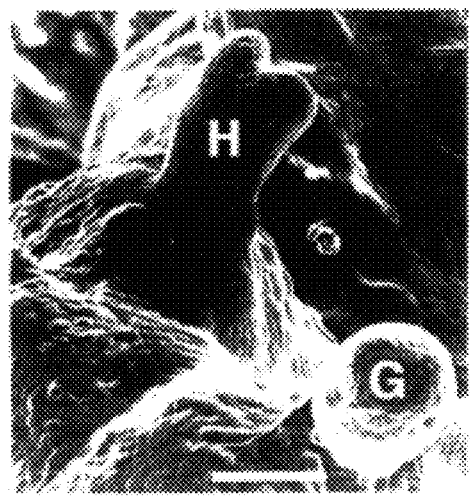
Figure 3C:
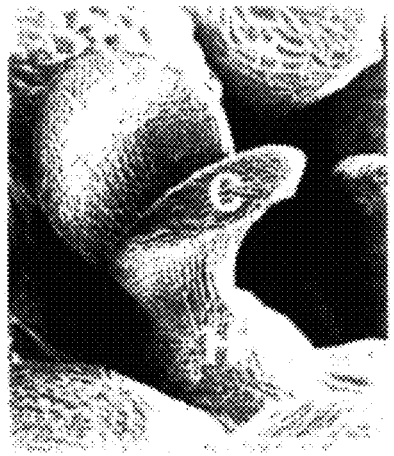
Figure 3D:
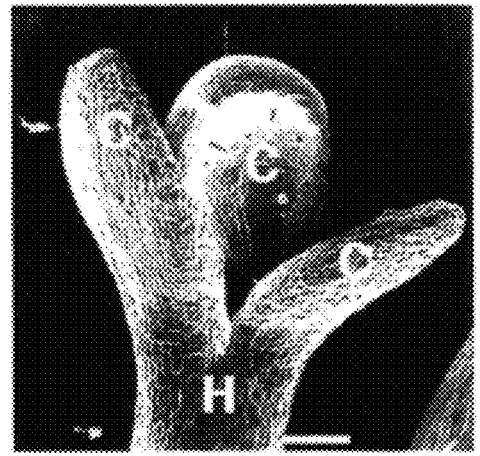

The Development of pga6 Somatic Embryos Morphologically and Temporally Resembles that of Zygotic Embryos To more closely follow the somatic embryogenesis process of the pga6 mutant, we performed a scanning electron microscopic analysis. Somatic embryogenesis in the inducer-treated pga6 explants highly resembled zygotic embryogenesis. The process was initiated from an asymmetric division of a single cell, giving rise to a smaller apical cell and a larger basal cell (FIG. 3A). Subsequently, embryo-like structures equivalent to that of zygotic embryos at the early globular stage were easily recognizable (FIG. 3B). These somatic embryos underwent a typical embryogenesis process, including the heart stage, the torpedo stage, and the cotyledon stage (FIGS. 3B and 3C), and eventually germinated into healthy seedlings (FIG. 2F). In addition to the relatively normal growth and development of the somatic embryo-derived mutant plants, we observed that a small fraction (approximately 10%) of somatic embryos generated seedlings with three cotyledons (FIG. 3D). This abnormality is presumably caused by different expression levels of the PGA6 gene or by abiotic effects as occasionally observed in seedlings germinated from wild-type seeds. Nevertheless, these above results demonstrated that a conditional gain-of-function mutation in the pga6 locus promoted vegetative-to-embryonic transition, leading to the initiation of somatic embryogenesis.

EXAMPLE 7

Plant Hormone-Independent Somatic Embryo Formation

The data described above were obtained under tissue culture conditions. To investigate the effects of the pga6 mutation on normal plant growth and development, T1 seeds were germinated on MS media (Murashige and Skoog, 1962) with or without the inducer. No detectable abnormality in growth and development (phenotype) was observed in pga6 plants germinated and grown in the absence of the inducer. On the inductive MS medium, progeny with the mutant and wild-type phenotype segregated in the ratio of 3:1, characteristic of a dominant mutation in a single locus. Compared to wild-type seeds, the pga6 mutant seeds germinated substantially later, with a delay of 3-5 days, suggesting an inhibitory effect of the mutation on plant growth and development. Whereas approximately one third of the mutant seedlings stopped further growth after germination and eventually died, the remaining two thirds mutant seedlings rapidly turned into green calli upon germination. These two distinctive mutant phenotypes, with an approximately 2:1 ratio, were presumably due to segregations (heterozygous or homozygous) for the pga6 gain-of-function mutation locus, leading to different PGA6 expression levels in homozygous and heterozygous seedlings. This notion was supported by subsequent genetic analysis of the T2 generation derived from T1 plants grown under non-inductive conditions. Whereas all progenies of the putative homozygous T2 families (5 out of 16) showed only the "lethal" phenotype on the inductive medium, the remaining 11 heterozygous families gave rise to a typical 2:1:1 segregation for embryogenic calli, "lethal" and wild-type phenotypes. In addition, the strength of the mutant phenotype was dependent on the inducer concentrations and the induced PGA6 expression levels per se (see FIGS. 5B-C).

Figure 4E:
Figure 4F:
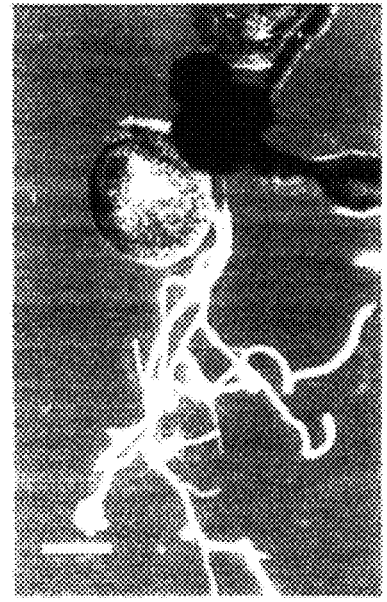
Figure 4G:
Figure 4H:

In the absence of any external plant hormones, somatic embryos were formed from green embryogenic calli (FIGS. 4B and 4C), which were able to germinate and grow normally into fertile adult plants (FIG. 4D). Interestingly, a considerably higher frequency of embryogenic callus formation was observed from excised pga6 roots cultured on the inductive MS medium (FIGS. 4G and 4H), suggesting the presence of an antagonistic activity to PGA6 in intact plants, which may promote post-embryogenesis growth and development.

Overexpression of LEC1 leads to abnormal plant growth and development as well as the occasional formation of embryo-like structures (Lotan et al., 1998). The LEC1 gain-of-function phenotype, however, appeared to be strictly restricted to developmental stages prior to germination. After seedling germination, overexpression of LEC1, controlled by the XVE inducible expression system (Zuo et al., 2000a), did not produce any apparent abnormality in plant growth and development, although the LEC1 transgene was highly responsive to the inducer during post-germination stages. On the other hand, the same transgenic line showed a strong phenotype if germinated directly in the presence of the inducer and the LEC1 transgene was highly responsive to the inducer during post-germination stages. These observations suggest that embryo- or seed-specific co-factor(s) are required for LEC1 function. To examine if PGA6 function is also dependent on embryo- or seed-specific co-factors, pga6 mutant seedlings at different growth stages, germinated and grown on the non-inductive MS medium, were transferred onto an inductive MS medium. At these developmental stages, the fate of both root and shoot stem cells has already been highly specified in wild-type plants. The pga6 mutation, however, appeared to reverse the developmental program, causing both root and shoot meristems to transform into embryogenic calli (FIG. 4D). Similar to that shown before, these embryogenic calli were eventually capable of forming somatic embryos, which were able to germinate and grow into morphologically normal adult plants. The above results strongly suggest that PGA6 plays a key role in specifying and maintaining embryonic cell identity, independent of any embryo- or seed-specific co-factors.

EXAMPLE 8

PGA6 is Identical to the Homeodomain Protein WUS

Figure 5A:
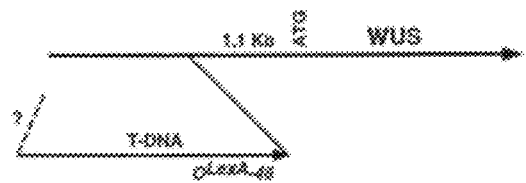
FIGS. 5A-D show that the pga6 phenotype is due to the inducer-dependent overexpression of WUS.
Figure 6A:
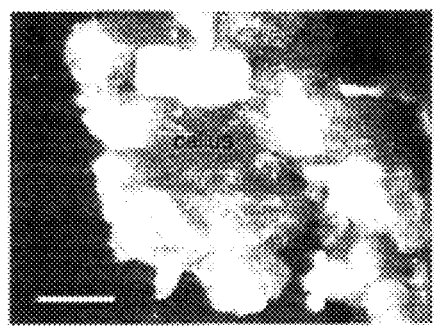
FIGS. 6A-H are photographs showing that 35S- or XVE-controlled overexpression of WUS cDNA phenocopies the pga6 phenotype.
Figure 6B:
Figure 6C:
Figure 6D:
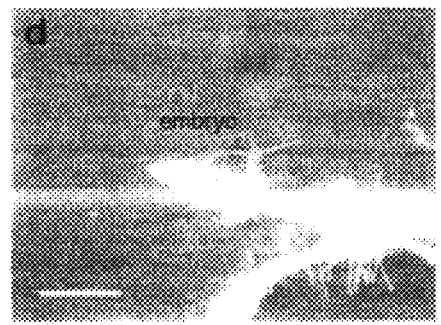
Figure 6E:
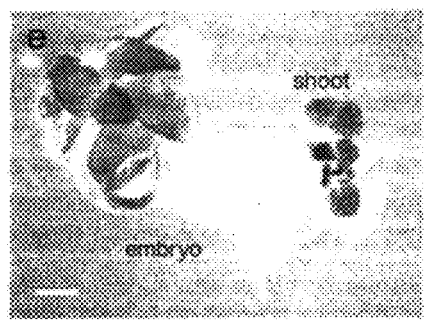
Figure 6F:
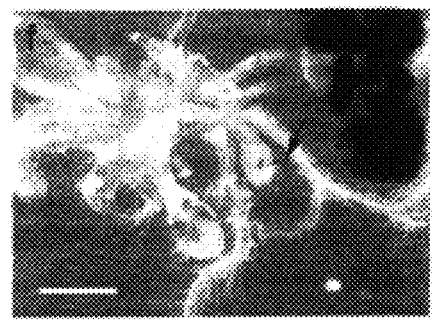

Based on the segregation of the kanamycin selectable marker, the pga6 mutant genome appears to contain a single transgenic locus. However, molecular analysis indicated the presence of the $O^{LexA}$-46 promoter in two independent loci. One $O^{LexA}$-46 promoter was found to fuse to the WUS gene in chromosome II (Mayer et al., 1998), approximately 1 kilobase-pair (Kb) upstream from the putative translation initiation codon (FIG. 5A). The second $O^{LexA}$-46 promoter fused immediately upstream of the putative translation initiation codon of an open reading frame (ORF) in chromosome V, encoding a putative basic-helix-loop-helix type transcription factor (deigned ORF1). To verify the identity of the PGA6 gene(s), cDNA fragments containing both WUS and the putative ORF1 were cloned into an XVE vector, and the resulting constructs were used to transform wild-type plants (Bechtold et al., 1993). Explants derived from XVE-ORF1 T1 transgenic plants did not show any apparent inducer-dependent phenotype. In addition, ORF1 expression did not appear to be up-regulated by the chemical inducer in pga6 plants, presumably due to the instability of the ORF1 transcript lacking the entire 5'-untranslated region (UTR). By contrast, all pga6 mutant phenotypes as described before were observed in the XVE-WUS T2 transgenic plants (FIGS. 6A and 6B) in an inducer-dependent manner (see Example 11 for details).

Figure 5B:
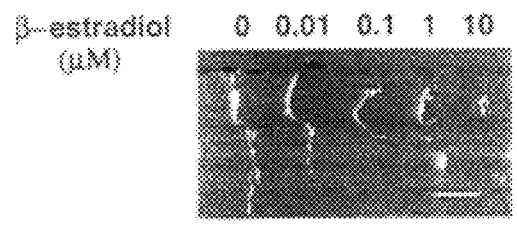
Figure 5C:
Figure 5D:
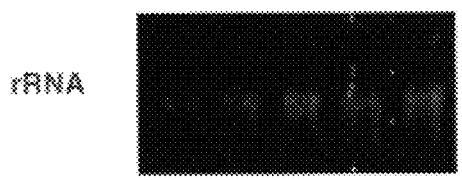

WUS expression was strictly dependent on different concentrations of the inducer in pga6 mutant plants (FIG. 5B). FIG. 5C shows expression of PGA6/WUS induced by different concentrations of the inducer. Ten-day-old pga6 seedlings germinated and grown on the MS medium were transferred to an MS medium containing various concentrations of 17-β-estradiol as indicated and cultured for an additional 16 hours before total RNA extraction. Five µg total RNA were used for Northern blot analysis using a WUS cDNA fragment as a probe. Consistent with the inducer concentration-dependent WUS expression, pga6 plants also showed various penetrations of the mutant phenotype in an inducer concentration-dependent fashion (FIG. 5B), thus providing a series of conditional mutant alleles for further functional studies.

Figure 6G:
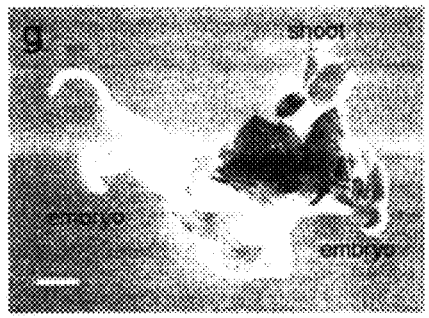
Figure 6H:
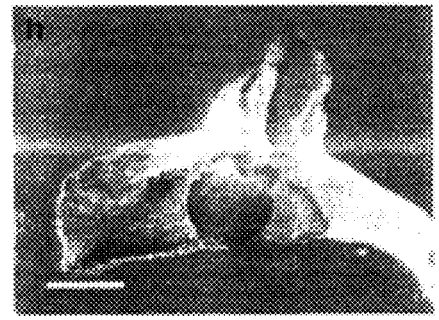

We also used a 35S-WUS construct for transformation of *Arabidopsis thaliana* Columbia as well as Landsberg ecotype. Most of the transformants recovered from selection showed strong alteration in seedling development. The hypocotyl was swollen and root tips often enlarged to give rise to shoot-like or embryo-like structures which were unable to further develop (FIGS. 6C-G). Leaf development, when observed, was also compromised indicating strong alteration of the shoot apical meristem (SAM) which, besides lateral organs, could also form adventitious shoots or embryo-like structures (FIGS. 6G-H). Overall, all the tissues of the transformants would give rise to organs or embryo-like structures whose further development, however, was impaired. This observation supports the validity of our strategy of using an inducible system to isolate genes involved in the switch to embryo development as the continuous overexpression of regulatory proteins would prevent recovery of the mutants.

In summary, the above results indicated that the $O^{LexA}$-46 promoter-tagged WUS in the mutant genome represents PGA6. We will refer to the PGA6 gene/protein as WUS in the future, but use pga6 for the mutation/mutant identified in this study due to different properties between the loss- and gain-of-function mutations.

Because the $O^{LexA}$-46 promoter fused approximately 1 Kb upstream from the putative translation start codon (FIG. 5A), the WUS promoter presumably remains functional in the mutant genome, leading to no apparent loss-of-function phenotype for the mutation. Nevertheless, the WUS gene was strongly inducible, giving rise to two transcripts, approximately 1.3 and 2.3 Kb (FIG. 5C). The shorter transcript was presumably generated from the native transcription initiation site of the WUS gene, in which case the LexA operator sequence might serve as an enhancer to the WUS promoter. On the other hand, the longer transcript might represent transcription from the $O^{LexA}$-46 promoter. This suggests that the $O^{LexA}$-46 sequence can serve as a functional promoter, as well as a transcriptional enhancer for activation tagging.

EXAMPLE 9

WUS Represses LEC1 Expression During Embryogenesis

Figure 7A:
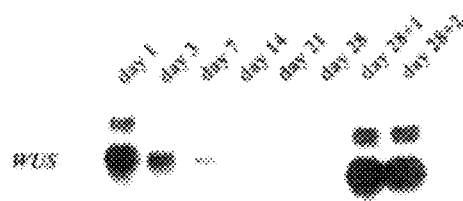
FIGS. 7A-C are Northern blots of RNA from root explants prepared from pga6 seedlings cultured on the screening medium (SCM) for different times as indicated. On day 28, when somatic embryos were apparent, cultures were transferred onto a freshly-prepared SCM or control medium (SCM without the inducer) and incubated for an additional day (28+1) or two days (28+2). Five micrograms of total RNA, prepared from the frozen materials, were analyzed by Northern blotting using WUS (FIG. 7A) and LEC1 (FIG. 7B) cDNA as probes. The blot was rehybridized with an actin cDNA probe (FIG. 7C) to ensure that equal amounts of RNA were loaded.

The above data indicate that WUS, in addition to its meristem function described previously (Laux et al., 1996; Mayer et al., 1998), also plays a critical role in promoting or maintaining the embryonic potential. We have investigated expression of several embryo- or seed-specific genes in pga6 embryogenic callus and somatic embryos. Root explants derived from pga6 mutant plants were cultured on an MS medium supplemented with the inducer. Under such conditions, whereas embryogenic calli appeared after 10-15 days, somatic embryos and germinating seedlings were generated after 20 days (see FIGS. 2A-F, 3A-D and 4A-H). Due to the transient expression nature of the XVE inducible system (Zuo et al., 2000a), WUS expression gradually declined upon continued culture on the inductive medium; however, the expression can be strongly re-induced by adding freshly-prepared inducer (FIG. 7A).

Figure 7B:
Figure 7C:

The LEC1 gene, normally expressed only in embryos and seeds (Lotan et al., 1998), was highly expressed in 20-30-day-old explants, a stage when somatic embryos and derived seedlings were generated. FIG. 7B shows LEC1 expression from 14 days until 28 days when pga6-dependent somatic embryogenesis takes places. LEC1 expression, however, was dramatically decreased upon reactivation of WUS expression (FIG. 7B). No alteration of LEC1 expression was detected when the explants/calli were transferred onto the control medium for an additional two days, suggesting that the LEC1 repression was a specific response to the 17-β-estradiol induced WUS expression.

These observations suggest that LEC1 expression in pga6 explants was not a direct response to WUS overexpression but rather a consequence of the pga6 somatic embryo development. On the other hand, a developmental path redefined by WUS overexpression leads to the repression of LEC1, a gene presumably involved in embryo maturation.

EXAMPLE 10

Enhanced Frequency of Somatic Embryo Formation by Addition of 2,4-D

Although we were able to generate somatic embryos from various pga6 tissues/organs in the absence of any external hormone, the frequency of somatic embryo formation appears to be lower compared to that observed in our original screening conditions, under which a 2,4-D pretreatment was included. To test the effects of 2,4-D on somatic embryogenesis, pga6 root explants were cultured on MS medium with 0.5 mg/L 2,4-D for 5 days prior to being transferred to an MS medium with or without 10 μM 17-β-estradiol. No somatic embryo formation was observed in the medium without the inducer, whereas numerous somatic embryos were generated after 2-3 weeks culturing in the presence of the inducer. As shown above (see Example 7 and FIGS. 4A-H) and by the results disclosed in this Example, the absence of 2,4-D pretreatment resulted in a substantially decreased efficiency for somatic embryo formation, indicating that the 2,4-D treatment is able to significantly increase the efficiency of somatic embryo formation. Collectively, the above results suggest that 2,4-D was able to enhance yet unidentified components in the signaling network, which play a key role in promoting the vegetative-to-embryonic transition. In addition, these results further demonstrated the validity of our working hypothesis as well as the screening strategy, i.e., that external hormones alone were incapable of activating key components for the vegetative-to-embryonic transition in *Arabidopsis*, and that the appropriate external hormone treatment in combination with gain-of-function mutations in key regulatory genes is fully capable of promoting the vegetative-to-embryonic transition or somatic embryogenesis.

EXAMPLE 11

Somatic Embryo Formation of Explants Derived from Transgenic Plants Carrying a pER10-WUS Transgene The XVE vector pER10 is identical to pER 8 except that the hygromycin resistance marker is replaced with a kanamycin-resistance marker (Zuo et al., 2000(a)). Full length WUS cDNA was placed under the control of the XVE system in pER10. Stem segments derived from the pER10-WUS transgenic plants were pre-cultured on the MS medium with 0.5 mg/L 2,4-D for 5 days and then transferred to an MS medium with or without 10 μM 17-β-estradiol. No somatic embryo was observed in medium in the absence of the inducer, whereas with the inducer, many somatic embryos were generated after 2-3 weeks of culture.

Similar to that of pga6 mutant plants, we found that the 2,4-D pre-treatment substantially increased the frequency of somatic embryo formation in pER10-WUS transgenic plants.

The method of placing WUS in pER10 or similar vectors which can be regulated enables one to perform the same or similar experiments in plants other than Arabidopsis.

EXAMPLE 12

Placing WUS Under the Control of a Tissue Specific Promoter

The G10-90 promoter in the XVE vector can be replaced with a tissue-specific promoter (e.g. a pollen-, root-stem- or leaf-specific promoter). A variety of tissue specific promoters are well known to those of skill in the art. Because expression of a transgene is activated by the chimeric XVE gene which is controlled by a tissue-specific promoter in this Example, the $O^{LexA}$-46 promoter controlling the WUS transgene is therefore tissue-specific in an inducer-dependent manner. This means that WUS will be induced only in the presence of an inducer and only in the specific tissue corresponding to the tissue specific promoter. Appropriate tissues or cell types, can then be collected from the transgenic plants and used for induction of somatic embryos as described in Examples 10 and 11.

Particularly when pollen derived from transgenic plants carrying a pollen-specific promoter-XVE/$O^{LexA}$-46-WITS vector is used, progeny plants generated from pollen-derived somatic embryos should be haploid instead of diploid (see, e.g., Twell et al., 1989 and Twell et al., 1990 for pollen specific promoters). In this embodiment of the invention, a transgenic plant having in its genome a Wuschel (WUS) gene under the control of an inducible, pollen-specific promoter would not normally express the gene. Pollen from such a plant can be cultured in the presence of the inducer until somatic embryogenesis occurs, after which the inducer is removed and the haploid embryos are permitted to develop into haploid clones according to standard techniques.

EXAMPLE 13

Use of the pER10-WUS as a Silent Marker for Transformation

The pER10-WUS vector can be used directly for transformation of explants without the use of an antibiotic resistance marker. Somatic embryos that formed in the presence of an inducer but in the absence of cytokinin should be transformants, because under such conditions non-transformants will be incapable of forming somatic embryos nor shoots due to the lack of induced WUS gene expression. Upon inducer removal, the embryos and shoots will develop into normal and fertile plants. The vector can include any gene or genes which are desired to be present in the transformed plants and these can be under the control of a desired promoter. The plants selected as a result of selecting for inducible WUS expression-dependent somatic embryos or shoots will contain the desired gene or genes.

If desired, the WUS transgene can be placed into a vector comprising a means of removing the WUS transgene as well as other portions of the vector which are no longer desired, e.g., using the XVE-Cre/lox system (Zuo et al., 2001). Such methods are also disclosed in U.S. patent application Ser. No. 09/439,534, filed 12 Nov. 1999, which is incorporated herein by reference.

EXAMPLE 14

Figure 8A:
FIGS. 8A-B illustrate formation of somatic embryos from isolated zygotic embryos of PGA6 transgenic plants grown in the presence (FIG. 8A) or absence (FIG. 8B) of an inducer of PGA6.
Figure 8B:
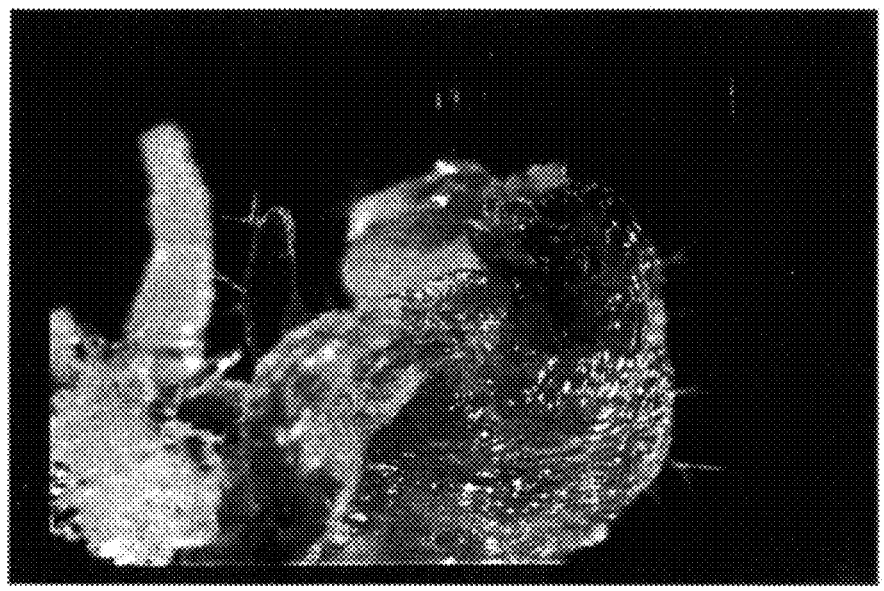

Induction of Formation of Somatic Embryos from Isolated Zygotic Embryos of PGA6 Transgenic Plants Zygote embryos at late heart stage were isolated from young siliques of PGA6 plants and transferred to either non-inductive medium (MICK: MS salts, 30 g/L sucrose, 0.15 mg/L IAA, 100 mg/L carbenicillin, 50 mg/L kanamycin, and 0.25% phytagel, pH 5.7) or inductive medium (MICK plus 10.0 μM 17-β-estradiol). After two weeks of culture, 10 zygotic embryos formed embryogenic calli on the inductive medium, but only 3 zygotic embryos started to form embryogenic calli on the non-inductive MICK medium. After 35 days of culture on the inductive medium, 10 zygotic embryos formed somatic embryos with a regeneration index (the number of somatic embryos per zygote embryo explant) of about 70-100 (FIG. 8A). By contrast, on MICK medium without estradiol, only two zygotic embryos regenerated somatic embryos and the somatic embryo regeneration index was about 10-20 (FIG. 8B).

EXAMPLE 15

Generating an Apomictic Plant

Apomixis can be induced by introducing WUS into a plant cell in such a manner that the WUS gene is expressed in the appropriate tissues (e.g., nucellus tissue). This can be by means of, but is not limited to, placing the WUS gene under the control of a tissue-specific promoter (e.g., a nucellus-specific promoter), an inducible promoter, or a promoter that is both inducible and tissue-specific. Inducing expression of the WUS gene, e.g. in the nucellus, produces apomixis leading to an apomictic plant. This plant may then be used to establish a true-breeding plant line. Additionally, the vector utilized to transfer WUS into the plant cell can include any other desired heterologous gene in addition to WUS, including but not limited to, a marker gene or a gene to confer a desirable trait upon the plant, e.g., a gene resulting in larger plants, faster growth, resistance to stress, etc. This would lead to the development of an apomictic line with the desired trait.

In a variation of the scheme, plant expression cassettes, including but not limited to monocot or dicot expression cassettes, directing WUS expression to the inner integument or nucellus can easily be constructed. An expression cassette directing expression of the WUS DNA sequences to the nucellus is made using the barley Nuc1 promoter (Doan et al., 1996). The expression is used for plant transformation. Other genes which confer desirable traits can also be included in the cassette.

It is anticipated that transgenic plants carrying the expression cassette will then be capable of producing de novo embryos from WUS expressing nucellar cells. In the case of maize, this is complemented by pollinating the ears to promote normal central cell fertilization and endosperm development. In another variation of this scheme, Nuc1:WUS transformations could be done using a fie (fertility-independent endosperm)-null genetic background which would promote both de novo embryo development and endosperm development without fertilization (Ohad et al., 1999). Upon microscopic examination of the developing embryos it will be apparent that apomixis has occurred by the presence of embryos budding off the nucellus. In yet another variation of this scheme the WITS DNA sequences could be delivered as described above into a homozygous zygotic-embryo-lethal genotype. Only the adventive embryos produced from somatic nucellus tissue would develop in the seed.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Bashaw, Crop Science, 1980. 20: p. 112.

Bechtold, N., Ellis, J., and Pelletier, G., *In planta Agrobacterium-mediated gene transfer by infiltration of adult Arabidopsis thaliana plants*. C. R. Acad. Sci. Ser. III Sci. Vie, 1993. 316: p. 1194-1199.

Brand, U., Fletcher, J. C., Hobe, M., Meyerowitz, E. M., and Simon, R., *Dependence of stem cell fate in Arabidopsis on a feedback loop regulated by CLV3 activity*. Science, 2000. 289: p. 617-619.

Clark, S. E., *Cell signalling at the shoot meristem*. Nat. Rev. Mol. Cell Biol., 2001. 2: p. 276-284.

Doan, D. N., Linnestad, C. and Olsen, O. A., *Isolation of molecular markers from the barley endosperm coenocyte and the surrounding nucellus cell layers. Plant Mo. Biol.*, 1996. 31: p. 877-886.

Ishige, F., Takaichi, M., Foster, R., Chua, N.-H., and Oeda, K., *A G-box motif (GCCACGTGCC) tetramer confers high-level constitutive expression in dicot and monocot plants*. Plant J., 1999. 18:443-448.

Kakimoto, T., *CKI1, a histidine kinase homolog implicated in cytokinin signal transduction*. Science, 1996. 274: p. 982-985.

Koncz, C., Martini, N., Mayerhofer, R., Koncz-Kalman, Z., Korber, H., Redei, G. P., and Schell, J., *High-frequency T-DNA-mediated gene tagging in plants*. Proc. Natl. Acad. Sci. USA, 1989. 86(21): p. 8467-8471.

Laux, T., Mayer, K. F., Berger, J., and Jurgens, G., *The WUSCHEL gene is required for shoot and floral meristem integrity in Arabidopsis*. Development, 1996. 122: p. 87-96.

Lin, X., Hwang, G. J, and Zimmerman, J. L., *Isolation and characterization of a diverse set of genes from carrot somatic embryos*. Plant Physiol., 1996. 112: p. 1365-1374.

Liu, Y. G., Mitsukawa, N., Oosumi, T., and Whittier, R. F., *Efficient isolation and mapping of Arabidopsis thaliana T-DNA insert junctions by thermal asymmetric interlaced PCR*. Plant J., 1995. 8: p. 457-463.

Lotan, T., Ohto, M., Yee, K. M., West, M. A., Lo, R., Kwong, R. W., Yamagishi, K., Fischer, R. L., Goldberg, R. B., and Harada, J. J., *Arabidopsis LEAFY COTYLEDON1 is sufficient to induce embryo development in vegetative cells*. Cell, 1998. 93: p. 1195-1205.

Mayer, K. F., Schoof, H., Haecker, A., Lenhard, M., Jurgens, G., Laux, T., *Role of WUSCHEL in regulating stem cell fate in the Arabidopsis shoot meristem*. Cell, 1998. 95: p. 805-815.

Meinke, D. W., *A homoeotic mutant of Arabidopsis thaliana with leafy cotyledons*. Science, 1992. 258: p. 1647-1650.

Meinke, D. W., Franzmann, L. H., Nickle, T. C., and Yeung, E. C., *Leafy cotyledon mutants of Arabidopsis*. Plant Cell, 1994. 6: p. 1049-1064.

Mordhorst, A. P., Toonen, M. A. J., and de Vries, S. C., *Plant embryogenesis*. Crit. Rev. Plant Sci., 1997. 16: p. 535-576.

Mordhorst, A. P., Voerman, K. J., Hartog, M. V., Meijer, E. A., van Went, J., Koornneef, M., and de Vries, S. C., *Somatic embryogenesis in Arabidopsis thaliana is facilitated by mutations in genes repressing meristematic cell divisions*. Genetics, 1998. 149: p. 549-563.

Murashige, T., and Skoog, F., *A revised medium for rapid growth and bioassays with tobacco tissue culture*. Physiol. Plant, 1962. 15: p. 473-497.

Ohad, N., Yadegari, R., Margossian, L., Hannon, M., Michaeli, D., Harada, J. J., Goldberg, R. B., and Fischer, R. L., *Mutations in FIE, a WD polycomb group gene, allow endosperm development without fertilization*. The Plant Cell, 1999. 11: p. 407-416.

Parlevliet J E et al. Citrus. Proc. Am. Soc. Hort. Sci., 1959. 74: p. 252-260.

Pepin et al, Crop Science, 1971. 11: p. 445-448.

Rieger et al., in *Glossary of Genetics and Cytogenetics*, Springer-Verlag, New York, N.Y., 1976

Sambrook, J., Fritsch, E. F., and Maniatis, T., *Molecular cloning: A Laboratory Manual*. 1989, Cold Spring Harbor, N.Y.: Cold Spring Harbor Laboratory Press.

Schmidt, E. D., Guzzo, F., Toonen, M. A., and de Vries, S. C., *A leucine-rich repeat containing receptor-like kinase marks somatic plant cells competent to form embryos*. Development, 1997. 124: p. 2049-2062.

Schoof, H., Lenhard, M., Haecker, A., Mayer, K. F., Jurgens, G., and Laux, T., *The stem cell population of Arabidopsis shoot meristems in maintained by a regulatory loop between the CLAVATA and WUSCHEL genes*. Cell, 2000. 100: p. 635-644.

Skoog, F., and Miller, C. O., *Chemical regulation of growth and organ formation in plant tissues cultured in vitro*. Symp. Soc. Exp. Biol., 1957. 11: p. 118-131.

Spemann, H., and Mangold, H., *Uber Induktion von Embryonalanlagen durch Implantation artfremder Organisatoren*. Archiv fur Mikroskopische Anatomie and Entwicklungsmechanik, 1924. 100: p. 599-638.

Stone, S. L., Kwong, L. W. Yee, K. M., Pelletier, J., Lepiniec, L., Fisher, R. L., Goldberg, R. B., and Harada, J. J., *LEAFY COTYLEDON 2 encodes a B3 domain transcription factor that induces embryo development*. Proc. Natl. Acad. Sci. U.S.A., 2001. 98:11806-11811.

Sugiyama, M., *Organogenesis in vitro*. Curr. Opin. Plant Biol., 1999. 2: p. 61-64.

Sugiyama, M., *Genetic analysis of plant morphogenesis in vitro*. Int. Rev. Cytol., 2000. 196: p. 67-84.

Thomas, T. L., *Gene expression during plant embryogenesis and germination: an overview*. Plant Cell, 1993. 5: p. 1401-1410.

Twell, D., Wing, R. Yamaguchi, J. and McCormick S. *Isolation and expression of an anther-specific gene from tomato*. Mol. Gen. Genet., 1989. 217: p. 240-245.

Twell, D. Yamaguchi, J. and McCormick, S. *Pollen-specific gene expression in transgenic plants: coordinate regulation of two different tomato gene promoters during microsporogenesis*. Development, 1990. 109: p. 705-713.

Waites, R., and Simon, R., *Signaling cell fate in plant meristems: Three clubs on one tousle*. Cell, 2000. 103: p. 835-838.

Wilson et al, Proceedings of the International Workshop on Apomixis in Rice, Changsha, People's Republic of China, Jan. 13-Jan. 15, 1992. Hunan Hybrid Rice Research Center, Changsha, People's Republic of China.

Wu, Y., Haberland, G., Zhou, C., and Koop, H.-U., *Somatic embryogenesis, formation of morphogenetic callus and normal development in zygotic embryos of Arabidopsis thaliana in vitro*. Protoplasma, 1992. 169: p. 89-96.

Zimmerman, J. L., *Somatic embryogenesis: A model for early development in higher plants*. Plant Cell, 1993. 5: p. 1411-1423.

Zuo, J., Niu, Q.-W., and Chua, N.-H., *An estrogen receptor-based transactivator XVE mediates highly inducible gene expression in transgenic plants*. Plant J., 2000a. 24: p. 265-273.

Zuo, J., Niu, Q.-W., Nishizawa, N., Wu, Y., Kost, B., and Chua, N.-H., *KORRIGAN, an Arabidopsis endo-1,4-b-glucanase, localizes to the cell plate by polarized targeting and is essential for cytokinesis*. Plant Cell, 2000b. 12(7): p. 1137-1152.

Zuo, J., Niu, Q.-W, Moller, S. G., and Chua, N.-H., *Chemical-regulated, site-specific DNA excision in transgenic plants*. Nat. Biotechnol., 2001. 19. p. 157-161.

PATENTS AND PATENT APPLICATIONS

Published Patent Application WO 00/24914, published 4 May 2000.
Published Patent Application WO 01/23575, published Apr. 5, 2001.
U.S. Pat. No. 5,710,367
U.S. Pat. No. 5,811,636
U.S. Pat. No. 6,028,185
U.S. Pat. No. 6,229,064
U.S. Pat. No. 6,239,327

What is claimed is:

1. A method for producing a haploid plant comprising
(a) stably transforming a plant cell with a DNA molecule comprising at least one Wuschel coding sequence under the control of a promoter to produce a transgenic plant cell, wherein the promoter is selected from the group consisting of a haploid tissue specific promoter, an inducible promoter and a promoter that is both haploid-tissue specific and inducible, wherein the Wuschel coding sequence is the coding sequence of SEQ ID NO:12;
(b) generating a transgenic plant from said transgenic plant cell, (c) overexpressing the Wuschel coding sequence in a haploid tissue of said transgenic plant to produce a haploid somatic embryo, (d) growing said embryo into a haploid plant.

2. The method of claim 1, wherein the promoter is a haploid tissue specific promoter.

3. The method of claim 2, wherein the promoter is a pollen-specific promoter, and the haploid tissue of the transgenic plant is pollen.

4. The method of claim 2, wherein the promoter is an ovule-specific promoter, and the haploid tissue of the transgenic plant is ovule tissue.

5. The method of claim 1, wherein the promoter is an inducible promoter.

6. The method of claim 1, wherein the promoter is both haploid-tissue specific and inducible.

7. The method of claim 6, wherein the promoter is pollen-specific, and the haploid plant cell is a pollen cell.

8. The method of claim 5, wherein the haploid tissue is excised haploid tissue, the overexpressing step (c) is achieved in excised haploid tissue cultured in the presence of the inducer specific for the inducible promoter, for a time sufficient to induce formation of the haploid somatic embryo, followed by withdrawal of the inducer, and further wherein the growing step (d) is carried out in the absence of the inducer.

* * * * *